United States Patent [19]
Soares

[11] Patent Number: 5,261,923
[45] Date of Patent: Nov. 16, 1993

[54] METHOD AND APPARATUS FOR CONTINUOUS CIRCULAR CAPSULOREHEXIS

[76] Inventor: Christopher J. Soares, 4713 Willowbend, Houston, Tex. 77035

[21] Appl. No.: 872,442

[22] Filed: Apr. 23, 1992

[51] Int. Cl.⁵ .............................................. A61F 9/00
[52] U.S. Cl. .................................. 606/166; 606/170; 606/180
[58] Field of Search .............. 30/164.95, 388, 389, 30/505; 33/19.3; 604/294; 606/167, 170, 166, 172, 107, 180

[56] References Cited

U.S. PATENT DOCUMENTS

| | | | |
|---|---|---|---|
| 873,100 | 12/1907 | Skalstad | 33/102 |
| 1,043,408 | 11/1912 | De Vilbiss | 606/172 |
| 1,124,552 | 1/1915 | Suggs | 30/388 |
| 4,336,805 | 1/1982 | Smirmaul | 606/180 |
| 4,423,728 | 1/1984 | Lieberman | 606/180 |
| 4,708,138 | 11/1987 | Pazandak | 606/107 |
| 4,888,015 | 12/1989 | Domino | 606/107 |

FOREIGN PATENT DOCUMENTS

| | | | |
|---|---|---|---|
| 59056 | 9/1941 | Denmark | 30/388 |
| 380732 | 5/1940 | Italy | 30/388 |

Primary Examiner—C. Fred Rosenbaum
Assistant Examiner—Noelle Kent Gring

[57] ABSTRACT

A surgical instrument adapted to pass through a superior limbal incision and fit behind the cornea for making a continuous circular incision about the anterior pole of the lens capsule in extracapsular cataract extractions and phacoemulsification. The surgical instrument includes a rotating blade disposed at one end and adapted to rotate about 360°. The instrument is fixed with respect to the lens capsule by a peg extending from the rotation axis of the blade. A method for making the circular incision is also disclosed.

12 Claims, 3 Drawing Sheets

METHOD AND APPARATUS FOR CONTINUOUS CIRCULAR CAPSULOREHEXIS

FIELD OF THE INVENTION

This invention relates to a method and apparatus for making surgical incisions in tissue and particularly to a method and surgical instrument for use in extracapsular cataract extractions and phacoemulsification.

BACKGROUND OF THE INVENTION

A cataract is an occlusion of tissue comprising the lens in the eye. The lens, enclosed in a capsule, is situated immediately behind the pupil (FIG. 1), in front of the vitreous body, and encircled by the ciliary processes, which slightly overlap its margin.

The capsule of the lens is a transparent, highly elastic and brittle membrane, which closely surrounds the lens. It rests, behind, in the fossa petellaris in the fore part of the vitreous body; in front, it is in contact with the free boarder of the iris, this latter receding from it at the circumference, thus forming the posterior chamber of the eye; and it is retained in position chiefly by the suspensory ligament or zonules of the lens.

The lens is a transparent, bi-convex body, the convexity being greater in the posterior side than on the anterior side. The central points of its anterior and posterior surfaces are known as its anterior and posterior poles. It measures approximately 9 to 10 millimeters in the transverse diameter, and about 4 millimeters in the antero-posterior. It consists of concentric layers, of which the exterior are soft and easily detached (*substantia corticalis*); those beneath are firmer, the central ones forming a hardened nucleus (*nucleus lentis*). It is the clouding or opacity of these concentric layers which form the cataract.

In a cataract operation, the lens is removed from the eye (lens extraction). There are two principal types of lens extraction for cataracts in older patients—intracapsular and extracapsular. Intracapsular cataract extraction consists of removing the lens in its entirety through a 140°-160° superior limbal incision. In performing the intracapsular procedure, the time honored method has been to make a large limbal incision superiorly, grasp the lens with a metal capsule forceps and remove the lens intracapsularly. Later, a cryoprobe became a popular replacement for the metal forceps. In extracapsular cataract extractions, a superior limbal incision is also made, the anterior portion of the capsule is ruptured and removed, the nucleus is extracted, and the lens cortex is either irrigated or aspirated from the eye, leaving the posterior capsule behind.

In performing extracapsular cataract extractions, phacoemulsification and aspiration and phacofragmentation and irrigation procedures are commonly used. Using a small limbal incision, ultrasonic energy is used to break up the lens nucleus and cortex through an opening or hole in the anterior surface of the capsule. The rupturing of the anterior surface or wall of the capsule is made by piercing the wall with a cystitome, essentially a bent needle. In a procedure called "continuous circular capsulorehexis," the cystitome is used to make a small incision sufficient for forceps to grasp one side of the incision. Using forceps the anterior surface tissue of the capsule is torn in a circular fashion to produce a circular opening. In standard extracapsular cataract extractions not using phacoemulsification, the anterior capsule is removed, the corneo-scleral wound is opened to its full extent (8-10 mm) and the lens is removed from the eye. This removal can be done using a lens loop which scoops the lens and pulls it out of the capsule. Also, pressure (using a pair of forceps) can be applied to the surface of the eye inferiorly. This raises intravitreal pressure which delivers the lens through the wound opening.

In another technique, the cystitome is used to make perforations in a circular pattern about the anterior surface of the capsule and to the inside of the iris. Forceps are then used to tear the capsule tissue along the perforation.

Intracapsular cataract extraction, the old standard procedure for senile cataracts, presents the possibility of several serious post-surgical complications such as glacoma, retinal detachment, vitreous hemorrhage, infection, or epithelial downgrowth into the anterior chamber that prevents significant visual improvement.

A major disadvantage associated with each of the above capsulectomy techniques is that the direction of the tear is difficult to control. Structural weaknesses or imperfections in the capsule may cause the tear to be extremely irregular, even to the point where vitreous loss may occur. Use of the cystitome to perforate the capsule may initiate one or more stress tears, which when subjected to the tension of the tear, may deviate to a point where the integrity of the capsule jeopardizes the placement of an intraocular lens prothesis. At the very least, the capsulotomy tear produces an irregular boundary, making it difficult and time consuming to ascertain whether the intraocular lens prothesis has been properly positioned within the capsule.

SUMMARY OF THE INVENTION

In one form of the invention, the surgical instrument includes a blade adapted to rotate in a planar circle substantially parallel to the longitudinal axis of the instrument, thus making a circular incision in the tissue. A spike coincident with the rotation axis, maintains the location of the rotation axis with respect to the tissue.

In another form of the invention, the instrument includes an elongate housing having a first and second end defining a longitudinal axis. Transversely extending from the first end is a spike having one end retained within the housing and an opposite end forming a sharp point. Fixed to the spike and oriented substantially parallel to the housing is an arm adapted to rotate about the axis defined by the spike. Fixed to at least one end of the arm is a blade oriented substantially normal to the longitudinal axis of the housing. A shaft extending the length of the housing has a first end fixed with a gear adapted to engage a complementary gear about the spike within the housing. The opposite end of the shaft is fixed with a knurled handle or other means for rotating the shaft, which in turn moves the arm and blade in a circular fashion to make a circular incision in the tissue.

In another form of the invention, the handle includes a gear housing at one end and having dimensions no greater than the handle. A portion of the handle is adapted to receive a rotating blade within a recess so that the overall dimension of the handle is not exceeded. At one end of the handle, a cavity is formed and adapted to receive a worm gear fixed about a spike extending transversely through the end of the handle and fixed to the blade. A worm disposed at the end of a shaft extending the length of the handle meshes with the worm gear about the spike. Rotation of the shaft by a handle or other means rotates the blade about an axis substantially perpendicular to the longitudinal axis of the handle.

In one embodiment of the method using this invention, a relatively small superior limbal incision is made into the anterior chamber behind the cornea. The end of the instrument having the blade is inserted into the incision with the blade located beneath the handle. With the spike located substantially above the posterior pole of the lens capsule, the spike is used to perforate the capsule. Substantially simultaneously, the cutting element at the end of the blade engages the anterior surface of the capsule. With the blade fixed by the spike, the surgeon rotates the knurled handle to rotate the blade about the axis of the spike to make a circular incision. With the incision completed, the surgical instrument is removed together with the circular piece of tissue held by the spike. With the anterior surface of the capsule breach, conventional lens removal techniques and intraocular lens prothesis implant may be performed.

The advantages provided by this method and the instrument include a more expedient and efficient capsulorehexis procedure providing a significant reduction in radial tears of the capsule, good capsule integrity to receive the lens implant, hydrodissection of the lens, and a clean entry into the capsule for good implant placement. Ancillary advantages include a substantial reduction on erosion of the ciliary body and iris, lack of pupillary capture, and easy cortical clean up.

These and other objects, advantages, purposes and features of the invention will become more apparent from a study of the following description taken in conjunction with the drawings described below.

DETAILED DESCRIPTION OF THE PREFERRED EMBODIMENTS

Figure 6:
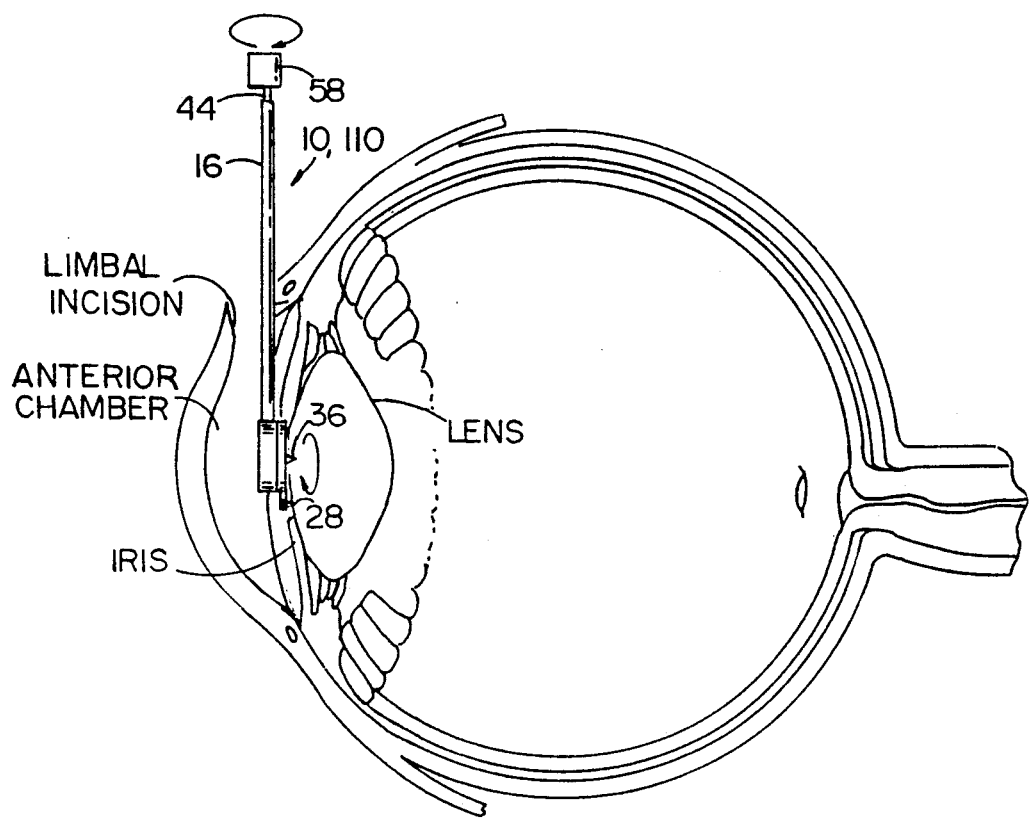
FIGS. 6 and 7 illustrate the application of this invention in performing a continuous circular capsulorehexis surgical technique.
Figure 7:
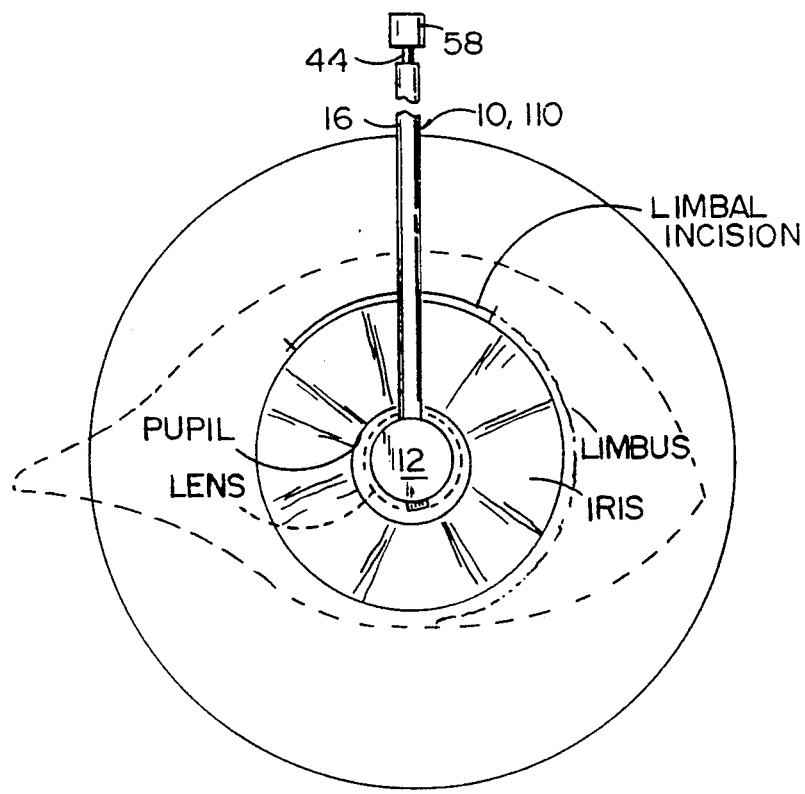

Referring to the drawing figures in detail, FIGS. 2-5 illustrate a preferred embodiment of the surgical instrument 10 of the invention including a disc-like housing 12 having a diameter D and height H to fit through a 4 to 7 millimeter superior limbal wound made in a human eye shown in FIGS. 6 and 7. Housing 12 is disposed at one end 14 of a handle 16 such that a longitudinal axis A—A passes through an opposite end 18 of handle 16, end 14 and the center 20 of disc-like housing 12. Dependent from a lower surface 22 of housing 12, and having a diameter substantially equal to and concentric with housing 12, is a blade 24 having a substantially circular form and an arm 26 radially extending therefrom. Disposed at the outer end of arm 26 and dependent therefrom is a cutting element 28. Blade 24 is rotationally coupled at its center 30 by a pin or axle 32 extending downwardly through center 20 of housing 12. Pin or axle 32 has a rounded head 34 at one end and a sharp point or spike 36 formed at the opposite end. Blade 24 is retained against housing 12 by a shoulder or pressure fit with the shaft 40. Shaft or shank 40 of pin 32 may have splines which are then pressure fit within the aperture passing through center 30 of blade 24. With blade 24 rigidly coupled to pin 32, the upper portion within housing 12 is free to rotate or journal about the pin axis within housing 12. In this fashion, blade 24 fits snugly against housing 12 to make an arcuate and stable circular rotation. The coupling of blade 24 to housing 12 is such that blade 24 is adapted to rotate in a circular plane about pin 32 and parallel to housing 12 and the longitudinal axis A—A of the instrument.

Figure 1:
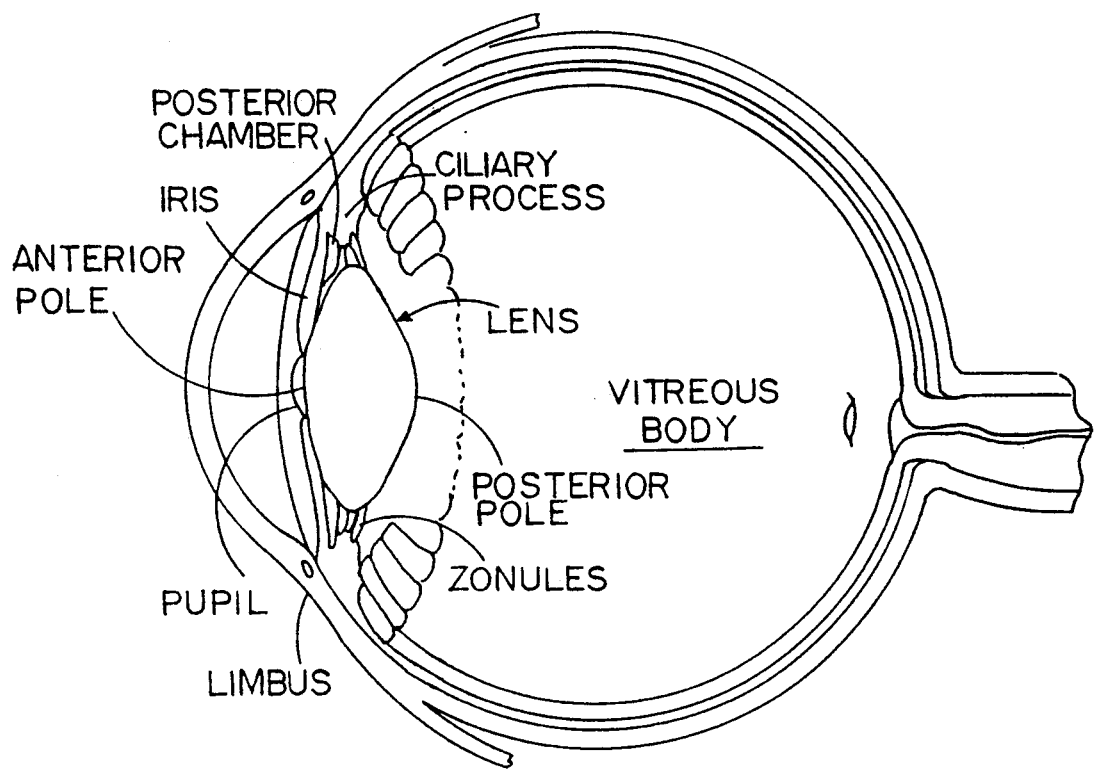
FIG. 1 is a sectional view of the human eye.
Figure 5:
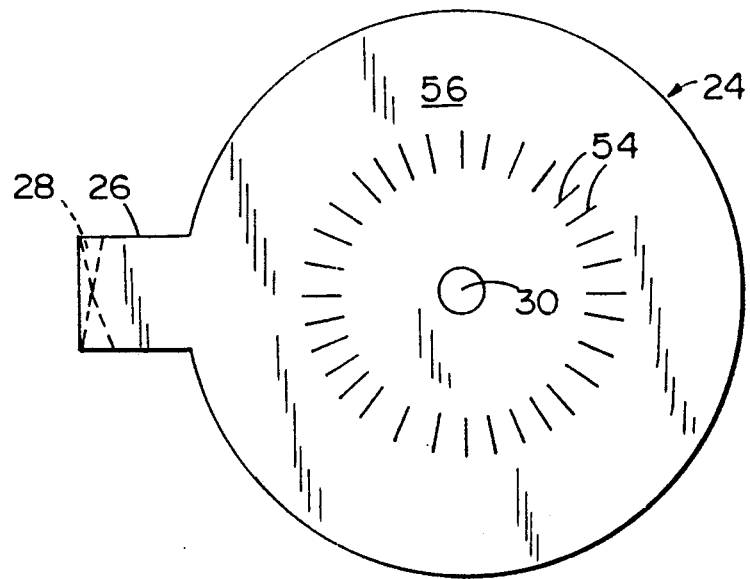
FIG. 5 is a plan view of one embodiment of a blade used in this invention.
Figure 2:
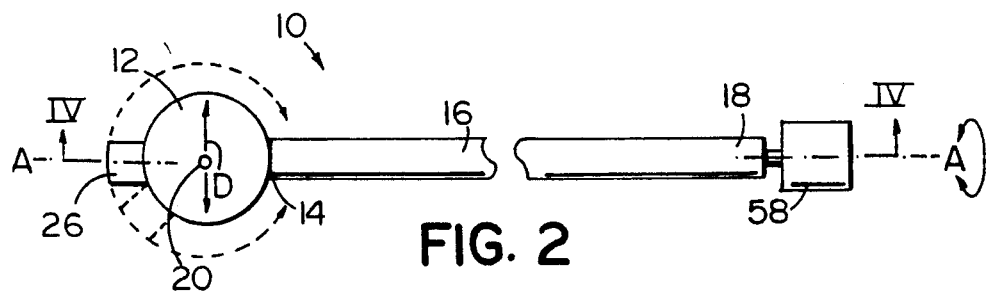
FIG. 2 is a plan view of the surgical tool of this invention.
Figure 3:
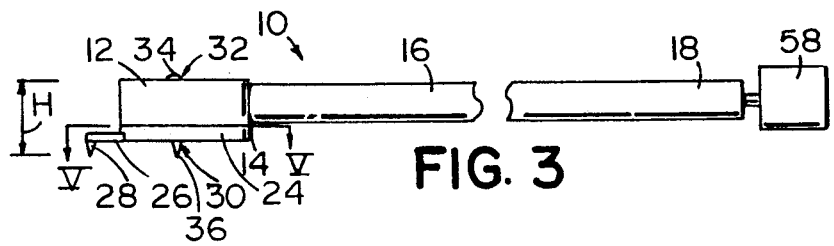
FIG. 3 is a side elevational view of the surgical tool of this invention.
Figure 4:
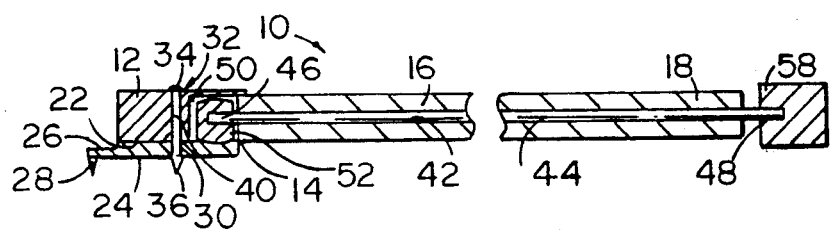
FIG. 4 is a bottom plan view of the surgical instrument of this invention.
Figure 8:
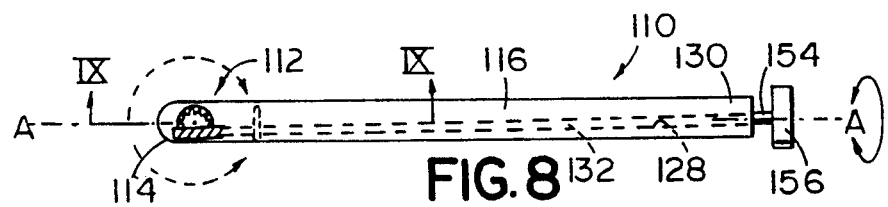
FIGS. 8-11 illustrate an alternate embodiment of the surgical instrument.
Figure 9:
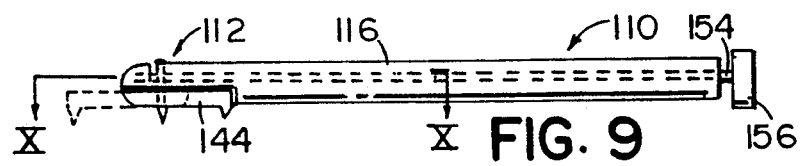
Figure 10:
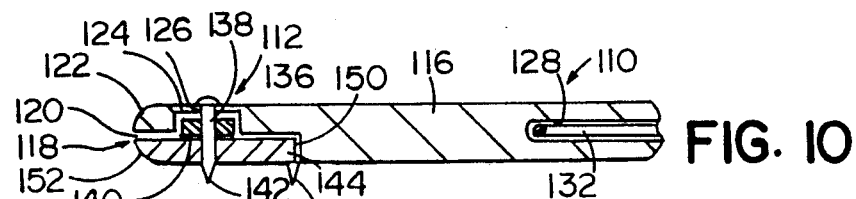
Figure 11:
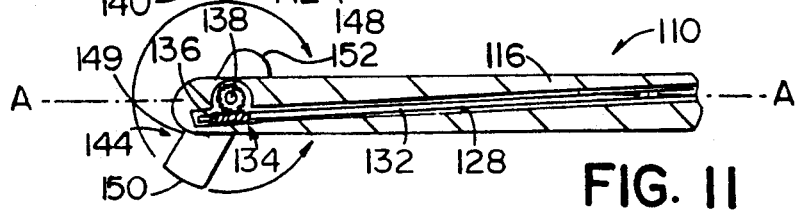

Handle 16 is preferably tubular, having a longitudinal and concentric passage 42 extending the entire length (FIG. 4). Passage 42 is adapted to receive a shaft 44 which extends the entire length of handle 16 with end portions 46 and 48 extending from opposite ends 14 and 18, respectively. End 46, extending within a recess or cavity 50, formed within housing 12, is received by and securely fastened to a pinion gear 52 adapted to rotate about the longitudinal axis A—A of shaft 44. The alignment of passage 42, shaft 44 and pinion gear 52 with respect to housing 12 is such that the cogs of gear 52 extend below the lower surface 22 of housing 12 to engage or mesh with cogs or gear slots 54 formed in the upper surface 56 of blade 24 adjacent surface 22. A knurled handle or knob 58, concentric with and rigidly fastened to opposite end 48 of shaft 44, is used to rotate shaft 44 and pinion gear 52, which in turn rotates blade 24 360° in either direction. Because cogs or slots 54 are distributed in a radial pattern about center 30 of upper surface 56 of blade 24 (FIG. 5), pinion gear 52 preferably has a frustoconical or spherical shape so as to provide a smooth meshing of the teeth with the cogs.

Instrument 10 may be molded from a rigid and high strength polymeric material so that instrument 10 may be used once and disposed of. The plastic could be recycled and repackaged in a sterile, tear-open container. Alternatively, the instrument may be made from surgical steel or other suitable material to provide a precision operation of the gear transmission and smooth rotation of the blade.

In operation, instrument 10 is intended to be used to make a continuous circular incision substantially about the anterior pole of the lens capsule, as shown in FIGS. 6 and 7. Typically in extracapsular cataract extractions, a superior incision between 4 and 7 millimeters is made along the limbus, the transition between the cornea and sclera. With blade 24 rotated so that cutting element 28 is positioned beneath handle 16, housing 12 is inserted through the incision such that the disc portion or diameter is oriented substantially parallel to the iris, being careful not to drag spike 36 across the eye. With the pupil dilated to its greatest extent, housing 12 is centered in the anterior chamber and above the anterior surface or pole of the lens capsule. With housing 12 appropriately located, instrument 10 is lowered so that spike 36 punctures the lens capsule and essentially seats housing 12 and blade 24 on the capsule. Substantially simultaneously with spike 36 puncturing the capsule, so does cutting element 28.

Once blade 24 has seated and breached the capsule, the surgeon rotates knurled knob 58, rotating blade 24 in a circular fashion about its center 30 fixed by spike 36. Cutting element 28 slices the tissue of the capsule until the circular incision is complete. The interior or inner portion of the incision is caught by spike 36 and removed from the anterior chamber upon withdrawal of instrument 10. With the anterior opening made in the capsule, phacoemulsification and aspiration or phacofragmentation and irrigation procedures may be used to remove the clouded cortex (substantia corticalis) and harder nucleus (nucleus lentis), leaving the remainder, posterior portion of the capsule intact to receive the intraocular lens prothesis. Also standard extracapsular extraction of the lens can be performed as described earlier.

The advantages provided by making the continuous circular incision or capsulorehexis using this invention include a significant reduction of radial tears of the capsule, capsule integrity to provide good centering or centration of the lens prothesis, safe hydrodissection and provides a clean entry into the capsule assuring that the lens implant is within the capsule. Ancillary advantages include a substantial reduction of ciliary body erosion
with improper lens implantation, lack of pupillary capture and iris erosion, and ease in cortial clean up.

Using the tool of this invention, the capsulorehexis may be made more expediently and efficiently with precision, thereby reducing the exposure of the wound to the environment and possible infection. The tool also enables capsulorehexis procedures for patients with poorly visualized capsules or small pupil openings.

FIGS. 8-11 illustrate an alternate embodiment of the invention 10. In this embodiment, housing 112 is integral with and of the same dimension as handle 116. A first end 114 of housing/handle 112, 116 is rounded to provide a gentle transition from the end to the thicker handle 116. Near end 114, a lower section 118 of housing 12 has been cut away and a transmission cavity 120 has been formed slightly to one side of longitudinal axis A—A in the upper portion 122. Cavity 120 is pierced at its upper end 124 by a hole 126 extending downwardly and concentric with cavity 120. Housing 112 and handle 116 also include a passage 128 extending the length thereof from a second end 130 and terminating adjacent cavity 120. The orientation of passage 128 may be at a slight angle to the longitudinal axis A—A in order to tangentially intercept cavity 120, or in the alternative, may parallel the axis A—A to be tangent to cavity 120.

Concentric with passage 128, and extending the length thereof, is a shaft 132 having a screw or worm 134 at one end and having one complete tooth or thread around the pitch surface. Worm 134 engages a worm gear 136 in cavity 120 about a pin 138 extending therein through hole 126. The lower portion of pin 138 below worm gear 136 may be supported within cavity 120 by a bearing 140. The lower portion of pin 138 preferably includes splines along its length and a sharp pointed spike 142 at its lower end.

A blade 144 is fixed to the lower portion of pin 138 by a tight pressure fit of a transverse hole 146 along the splined portion of the pin. Blade 144 is adapted to nest within cutout 118 and conform to the overall elongate shape with blade 144 aligned with housing 112 and handle 116. Blade 144 has a cutting element 148 dependent from one end 150 and a second end 152 which is shaped to conform to the rounded tip. The cutting element 148 is shaped so as to cut bi-directionally and has a length slightly greater than spike 138 in order to compensate for the curvature of the capsule's anterior surface.

Just as in the previous embodiment, the second end 154 of shaft 132 is fixed with a knurled handle 156 or other means for rotating the shaft about its longitudinal axis. Worm 134 at the opposite end rotates and causes worm gear 136 to rotate, which in turn rotates blade 144 in a circular plane perpendicular to pin 138 and parallel to housing 112 and handle 116.

In operation, cutting element 148 and arm 149 are positioned under handle 116 in cutout 118 to facilitate ingress into the wound. The surgeon centers spike 142 approximately above the anterior pole by referencing the top of pin 138 appearing through the top of housing 112. Once centered, tool 110 is lowered, causing spike 142 and cutting element 148 to breach the anterior surface of the capsule. The surgeon rotates knob 156 to rotate blade 144 and make the circular incision or capsulorehexis described above. Once the incision is complete, blade 144 is repositioned beneath the handle and removed, bringing the circular cutout portion of the capsule's anterior surface therewith.

Although the invention has been described with respect to specific embodiments thereof, many variations and modifications will become apparent to those skilled in the art. It is, therefore, the intention that the appended claims be interpreted as broadly as possible in view of the prior art to include all such various modifications.

The embodiments of the invention in which an exclusive property or privilege is claimed are defined as follows.

1. A surgical instrument for making a continuous circular incision about the anterior pole of a lens, comprising:
   a substantially disc-like housing adapted to fit within the anterior chamber behind the cornea;
   rotary means concentric with said disc-like housing adapted to rotate about an axis in a planar circle substantial parallel to said housing;
   a handle radially extending from said disc-like housing;
   means extending the length of said handle and adapted to engage said rotary means for rotating said rotary means in said planar circle;
   means concentric with said rotary means and extending perpendicular therefrom for piercing the anterior surface of said lens substantially close to said anterior pole for locating the rotation axis of said rotary means with respect to said lens; and
   cutting means extending perpendicular from said rotary means and distant from said piercing means for making a circular incision in the anterior surface of said lens substantially concentric about said piercing means.

2. A surgical instrument as recited in claim 1, wherein said rotary means includes:
   a substantially circular disc having an upper and a lower surface;
   a plurality of cogs radially defined in said upper surface and evenly spaced about the center of said circular disc; and
   means extending through the center of said disc for rotatably coupling said circular disc to said disc-like housing.

3. A surgical instrument as recited in claim 2, wherein said handle includes a first end rigidly attached to said housing and a second end radially spaced therefrom, said first and second end interconnected by a tubular passage concentric with the longitudinal axis of said handle.

4. A surgical instrument as recited in claim 3, wherein said means for rotating said rotary means includes:
- a shaft extending the length of said handle within said tubular passage and extending from said first and second end;
- a gear attached to a first end of said shaft within said housing and adapted to engage said plurality of cogs defined in said upper surface of said circular disc; and
- means attached to a second end of said shaft for rotating said shaft about its longitudinal axis.

5. A surgical instrument as recited in claim 4, wherein said piercing means includes a spike.

6. A surgical instrument as recited in claim 5, wherein said piercing means includes a blade having at least one cutting edge attached to said rotary means.

7. A surgical instrument as recited in claim 6, wherein said rotary means further includes an arm extending radially therefrom and having a distant end for retaining said blade.

8. A surgical instrument as recited in claim 1, wherein said rotary means includes an arm pivotally coupled to said housing and adapted to rotate in a planar circle and having a first end distant from said pivotal coupling to define the radius of said planar circle.

9. An instrument for making a circular incision in tissue, comprising:
- an elongate housing having a first and a second end and a cavity defined therein;
- a pin transversely extending from said housing at said first end having one end extending into said cavity and a point defined at an opposite end;
- a shaft extending along the longitudinal axis of said housing and having a first end adjacent said pin and an opposite end extending from said second end of said housing;
- an arm fixed to said pin extending from said housing and adapted to rotate in a plane parallel to said housing;
- means interconnecting said shaft and said pin for translating rotation of said shaft to rotary motion of said arm; and
- a blade fixed to said arm distant from an axis defined by said pin.

10. A method for breaching an orifice in an anterior surface of a lens capsule in the eye, comprising:
- making a superior limbal incision between 90° and 140°; and
- inserting a tool through said limbal incision and behind the cornea, to make a circular incision in the anterior surface of the capsule substantially about and enclosing the anterior pole, and within a boundary defined by the pupil of the iris.

11. The method as recited in claim 1, wherein the step of inserting said tool further comprises the step of fixing the location of said tool substantially above the anterior pole of said capsule.

12. The method as recited in claim 11, wherein fixing the location comprises the step of perforating said anterior surface of said capsule with a stake dependent from said tool to establish a center of the circular incision to be made in said anterior surface.

* * * * *